United States Patent [19]

Kawai

[11] Patent Number: 5,280,007
[45] Date of Patent: Jan. 18, 1994

[54] METHOD FOR SAFENING RICE AGAINST THE PHYTOTOXIC EFFECTS OF A SULFAMOYL UREA HERBICIDE

[75] Inventor: Kaiji Kawai, Toyohashi, Japan

[73] Assignee: American Cyanamid Company, Wayne, N.J.

[21] Appl. No.: 809,827

[22] Filed: Dec. 18, 1991

[51] Int. Cl.⁵ .............................. A01N 25/32
[52] U.S. Cl. ................... 504/105; 504/111; 504/212; 504/214
[58] Field of Search ....... 71/92, 93, 94, 120; 504/111, 105

[56] References Cited

U.S. PATENT DOCUMENTS

| | | | |
|---|---|---|---|
| 3,483,296 | 12/1969 | Martin et al. ................ | 71/120 |
| 4,272,283 | 6/1981 | Takematsu et al. ........... | 71/94 |
| 4,343,649 | 8/1982 | Sweetser ...................... | 71/93 |
| 4,465,509 | 8/1984 | Takematsu et al ............ | 71/119 |
| 4,515,620 | 5/1985 | Böhner ......................... | 71/91 |
| 4,584,010 | 4/1986 | Takeda et al. ................ | 71/92 |
| 4,622,065 | 11/1986 | Gemert ........................ | 71/93 |
| 5,009,699 | 4/1991 | Brady et al. ................. | 71/92 |

Primary Examiner—Allen J. Robinson
Assistant Examiner—B. Bembenick
Attorney, Agent, or Firm—Peggy A. Climenson

[57] ABSTRACT

There is provided a method for protecting a rice crop from injury caused by a sulfamoyl urea herbicide which comprises applying to the crop a non-phytotoxic antidotal amount of a compound selected from 1-(α,α,-dimethylbenzyl)-3-p-tolylurea and S-(1-methyl-1-phenylethyl)-1-piperidinecarbothioate.

20 Claims, No Drawings

METHOD FOR SAFENING RICE AGAINST THE PHYTOTOXIC EFFECTS OF A SULFAMOYL UREA HERBICIDE

BACKGROUND OF THE INVENTION

Sulfamoyl urea compounds and their use for the control of noxious plant species are described in U.S. Pat. Nos. 4,622,065 and 5,009,699, among others. This well-known class of herbicides, however, may cause injury to certain important agronomic crops.

The use of chemical antidotes to protect crops from injury due to sulfonyl urea herbicides is described in U.S. Pat. Nos. 4,343,649 and 4,584,010 and in Japanese Patents 61-112003, 62-263104 and 62-56406. However, there is no method described in the art to protect crop plants against injury due to the application of a sulfamoyl urea herbicide.

Therefore, it is an object of this invention to provide a method to safen rice, one of the world's most important economic crops, against the phytotoxic effects of the sulfamoyl urea class of herbicides.

SUMMARY OF THE INVENTION

The present invention is a method for the protection of a rice crop from injury caused by a herbicidally effective amount of a sulfamoyl urea herbicide of formula I

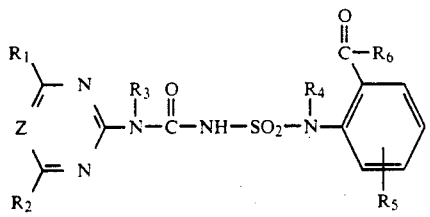

wherein
Z is N or CH;
$R_1$ and $R_2$ are each independently halogen, $C_1-C_6$ alkyl or $C_1-C_6$alkoxy;
$R_3$ and $R_4$ are each independently hydrogen, $C_1-C_6$ alkyl optionally substituted with one to three halogen or $C_1-C_4$alkoxy groups $C_2-C_4$ alkenyl and $C_2-C_4$alkynyl;
$R_5$ is hydrogen, halogen or $C_1-C_4$alkyl optionally substituted with one to three halogens and
$R_6$ is $C_1-C_6$alkyl or $C_3-C_6$cycloalkyl
which comprises applying an effective, non-phytotoxic antidotal amount of a compound selected from 1-($\alpha,\alpha$,-dimethylbenzyl)-3-p-tolylurea and S-(1-methyl-1phenylethyl)-1-piperidinecarbothioate.

DETAILED DESCRIPTION OF THE INVENTION

Rice is the most important food crop, and the major dietary component, for over one-third of the world's population. Rice production, to be efficient, entails the use of herbicides to control noxious plant species (weeds) which plague rice paddies. Improvements in controlling paddy field weeds are constantly being sought.

It has bow been found that weeds in rice paddy fields can be controlled without undue or unacceptable phytotoxicity (injury) to the rice plants by applying a combination of an herbicidally effective amount of a sulfamoyl urea compound of formula I with an antidotally effective amount of a compound selected from 1-($\alpha,\alpha$-dimethylbenzyl)-3-p-tolylurea and S-(1-methyl-1-phenylethyl)-1-piperidinecarbothioate.

Compounds of formula I which are especially effective when used in accordance with the method of invention are those wherein Z is CH; $R_1$ and $R_2$ are $C_1-C_6$ alkoxy; $R_3$, $R_4$ and $R_5$ are each hydrogen and $R_6$ is methyl, ethyl or cyclopropyl.

The compound 1-($\alpha,\alpha$-dimethylbenzyl)-3-p-tolylurea (daimuron) is a urea herbicide and cell division inhibitor and is described in The Pesticide Manual, 9th Edition, p. 221 (1991). The compound S-(1-methyl-1-phenylethyl)-1-piperidinecarbothioate (dimepiperate) is a thiocarbamate herbicide and is described in The Pesticide Manual, 9th Edition, p. 289 (1991). Surprisingly, when a sulfamoyl urea herbicide of formula I is applied in combination with a compound selected from daimuron or dimepiperate to either direct-seeded or transplanted rice at a weight ratio of about 1:2.5 to 1:150, preferably about 1:10 to about 1:50, weed control is effected with concomittant reduction of phytotoxicity to the rice plants. Either of the compounds may be applied in conjunction with the sulfamoyl urea herbicide as a combination composition or separately, either simultaneously or sequentially.

In actual practice, the sulfamoyl urea herbicide of formula I in combination with daimuron or dimepiperate may be applied to the surface of the water or to the foliage of the plants in a flooded paddy field. Application times may vary from about 4 days prior to sowing the rice seeds or transplanting the rice plants to about 5 days after sowing the rice seeds or transplanting the rice plants.

Both the formula I sulfamoyl urea herbicides and the antidotal compounds, daimuron and dimepiperate, may be applied as spray formulations or granular formulations. They may be applied as single agents, either simultaneously or sequentially or as a preformulated combination composition or may be premixed on location just prior to application.

In general, a herbicidally effective amount of a formula I compound is about 0.016-1.0 kg/ha, preferably about 0.02-0.5 kg/ha, more preferably about 0.02-0.2 kg/ha and most preferably about 0.04-0.06 kg/ha. The herbicidally effective amount will vary according to the condition of the field, the density of the weed population, the weather and the like. Similarly, the non-phytotoxic antidotally effective amount of daimuron or dimepiperate will vary depending on the field condition and the environment, however, when present in a weight ratio of herbicide to antidote of about 1:2.5 to 1:150, preferably about 1:10 to 1:50, phytotoxicity or injury to the rice plant will be reduced or eliminated.

In order to facilitate a more complete understanding of the invention, the following examples are presented. The examples are primarily for the purpose of illustrating more specific details of the invention and the invention is not to be limited thereby except as defined in the claims.

EXAMPLE 1

Evaluation of the safening effects of daimuron and dimepiperate on transplated rice against injury caused by a sulfamoyl urea herbicide under severe conditions Plastic pots, 100 cm² surface area and 9 cm in depth, containing diluvium paddy soil are flooded to the surface of the soil and the soil and water are stirred up (paddled) to a depth of 3 cm. Four rice plants at the 2.5-leaf stage are transplanted at a soil depth of 0.5 cm. Water is added to obtain a level of 4 cm above the surface of the soil and is maintained at that level throughout the test. Two days after transplanting, applications of the sulfamoyl urea herbicide, as a 0.2% granular formulation, alone and in combination with either daimuron as a 7% granular formulation or dimepiperate as an aqueous acetone solution are made. Two replicates of each test are run and no leaching is allowed to occur. After treatment, the plants are placed on greenhouse benches, watered such that the water level is maintained as stated above and cared for in accordance with conventional greenhouse practice. Observations are made at 30 days after treatment and phytotoxicity (plant injury) is evaluated on a 0–9 scale where 0 is no effect (no injury) and 9 is complete kill (100% injury). The sulfamoyl urea herbicide used is 1-{[o-(cyclopropylcarbonyl)phenyl]sulfamoyl}-3-(4,6-dimethoxy-2-pyrimidinyl)urea. The variety of rice used is Koshihikari. The results are averaged and shown in Table I.

TABLE I

Safening Effects Of Daimuron And Dimepiperate On Transplanted Rice Under Severe Conditions (0.5 cm depth)

| Antidotal Compound | Rate (kg/ha) | Plant Injury (Herbicide Rate, kg/ha) | | | |
|---|---|---|---|---|---|
| | | 0 | 0.02 | 0.06 | 0.18 |
| Daimuron | 0 | 0 | 3.0 | 5.0 | 5.5 |
| | 0.45 | 0 | 2.8 | 3.5 | 4.0 |
| | 0.90 | 0 | 2.5 | 2.8 | 4.0 |
| | 1.50 | 0 | 2.5 | 3.0 | 3.5 |
| Dimepiperate | 1.50 | 0 | 2.5 | 3.5 | 4.8 |
| | 3.00 | 0 | 1.5 | 2.3 | 5.0 |

EXAMPLE 2

Evaluation of the safening effects of daimuron and dimepiperate on transplanted rice against injury caused by a sulfamoyl urea herbicide and on the efficacy of said herbicide Pots, 200 cm$^2$ surface area and 15 cm in depth, containing diluvium paddy soil are flooded to the surface of the soil and the soil and water are paddled to a depth of 3 cm. Each pot is sown with fifty *Echinochloa crus-galli* seeds, five *Sagittaria pygmaea* tubers, four *Cyperus serotinus* tubers and fifty to sixty *Scirpus juncoides* seeds at a soil depth of 0–2 cm. After sowing, four rice plants at the 2.5-leaf stage are transplanted at a soil depth of 3 cm and four rice plants at the 2.5-leaf stage are transplanted at a soil depth of 0 cm in each pot. Water is added to obtain a water level of 4 cm above the soil surface and this water level is maintained throughout the test. Applications of the herbicide, both alone and in combination with either daimuron or dimepiperate, are made two days after transplanting and sowing. Two replicates of each test are run and no leaching is allowed to occur. After treatment, the plants are placed on greenhouse benches, watered such that the water level is maintained as stated above and cared for according to conventional greenhouse practice. Observations are made at 20 and 40 days after treatment (DAT) and plant injury is evaluated on a 0–9 scale where 0 is no effect (0% injury) and 9 is complete kill (100% injury). The sulfamoyl urea herbicide used is 1-{[o-(cyclopropylcarbonyl)phenyl]sulfamoyl}-3-(4,6-dimethoxy-2-pyrimidinyl)urea. The results are averaged and shown in Table II.

| Plant Species Used | |
|---|---|
| Column Heading | Scientific Name |
| Rice | *Oryza. sativa* |
| Ec | *Echinochloa crus-galli* |
| Sp | *Sagittaria pygmaea* |
| Cs | *Cyperus serotinus* |
| Sj | *Scirpus juncoides* |

TABLE II

Safening Effects Of Daimuron And Dimepiperate On Rice Injury And Herbicidal Efficacy Of A Sulfamoyl Urea Herbicide

| | | Plant Injury | | | | | | | | | | |
|---|---|---|---|---|---|---|---|---|---|---|---|---|
| | | Transplanted Rice | | | | Ec | | Sp | | Cs | | Sj | |
| | Rate | 3 cm | | 0 cm | | DAT | | DAT | | DAT | | DAT | |
| Application | kg/ha | 20 | 40 | 20 | 40 | 20 | 40 | 20 | 40 | 20 | 40 | 20 | 40 |
| Herbicide alone | 0.02 | 0.5 | 0 | 1.0 | 1.0 | 6.0 | 3.0 | 7.0 | 8.0 | 7.0 | 7.0 | 8.0 | 7.0 |
| | 0.04 | 1.0 | 0.5 | 2.0 | 2.0 | 6.0 | 4.0 | 7.0 | 8.0 | 8.0 | 8.0 | 8.0 | 8.0 |
| | 0.06 | 1.5 | 1.0 | 3.0 | 2.5 | 7.0 | 5.0 | 8.0 | 8.0 | 8.0 | 9.0 | 8.0 | 9.0 |
| | 0.12 | 2.0 | 2.0 | 5.0 | 3.0 | 8.0 | 7.0 | 8.0 | 8.0 | 8.0 | 9.0 | 9.0 | 9.0 |
| | 0.24 | 3.0 | 2.5 | 7.0 | 5.0 | | | | | | | | |
| Herbicide plus 1.0 kg/ha Daimuron | 0.02 | 0 | 0 | 0.5 | 0 | 7.0 | 6.0 | 7.0 | 7.5 | 8.0 | 9.0 | 9.0 | 9.0 |
| | 0.04 | 0 | 0 | 1.0 | 0.5 | 8.0 | 7.0 | 8.0 | 8.0 | 9.0 | 9.0 | 9.0 | 9.0 |
| | 0.06 | 0 | 0 | 1.3 | 1.0 | 8.0 | 8.0 | 8.0 | 8.0 | 9.0 | 9.0 | 9.0 | 9.0 |
| | 0.12 | 0 | 0 | 2.0 | 1.0 | 8.0 | 8.0 | 8.0 | 8.0 | 9.0 | 9.0 | 9.0 | 9.0 |
| | 0.24 | 0.5 | 0 | 2.8 | 2.0 | | | | | | | | |
| Herbicide plus 3.0 kg/ha Dimepiperate | 0.02 | 0 | 0 | 1.0 | 0.5 | 9.0 | 7.0 | 7.0 | 8.0 | 8.0 | 7.0 | 9.0 | 7.0 |
| | 0.04 | 0 | 0 | 2.0 | 1.0 | 9.0 | 8.0 | 8.0 | 8.0 | 8.0 | 8.0 | 9.0 | 8.0 |
| | 0.06 | 0 | 0 | 2.5 | 2.0 | 9.0 | 8.0 | 8.0 | 8.0 | 9.0 | 9.0 | 9.0 | 9.0 |
| | 0.12 | 0 | 0 | 3.5 | 2.5 | 9.0 | 9.0 | 8.0 | 8.0 | 9.0 | 9.0 | 9.0 | 9.0 |
| | 0.24 | 1.0 | 0.5 | 5.0 | 4.0 | | | | | | | | |
| Daimuron alone | 1.0 | 0 | 0 | 0 | 0 | 8.0 | 8.0 | 0 | 0 | 7.0 | 6.0 | 9.0 | 8.0 |
| Dimepiperate alone | 3.0 | 0 | 0 | 0 | 0 | 9.0 | 8.0 | 0 | 0 | 3.0 | 0 | 2.0 | 2.0 |
| Check (control) | | 0 | 0 | 0 | 0 | 0 | 0 | 0 | 0 | 0 | 0 | 0 | 0 |

EXAMPLE 3

Evaluation of the safening effects of dimepiperate on transplanted rice against injury caused by a sulfamoyl urea herbicide and on the efficacy of said herbicide Using essentially the same procedure described in Example 2 and substituting 1-{[o-(acetyl)phenyl]sulfamoyl}-3-(4,6-dimethoxy-2-pyrimidinyl)urea as the sulfamoyl urea herbicide, the following results are obtained and shown in Table III.

TABLE III

Safening Effects Of Dimepiperate On Rice Injury And Herbicidal Efficacy Of A Sulfamoyl Urea Herbicide

| | | Plant Injury | | | | | | | | | | |
|---|---|---|---|---|---|---|---|---|---|---|---|---|
| | | Transplanted Rice | | | | Ec DAT | | Sp DAT | | Cs DAT | | Sj DAT | |
| | Rate | 3 cm | | 0 cm | | | | | | | | | |
| Application | kg/ha | 20 | 40 | 20 | 40 | 20 | 40 | 20 | 40 | 20 | 40 | 20 | 40 |
| Herbicide alone | 1.00 | 5 | 5 | 8 | 8 | 8 | 9 | 8 | 9 | 8 | 9 | 9 | 9 |
| | 0.50 | 4 | 2 | 8 | 8 | 8 | 9 | 8 | 9 | 8 | 9 | 9 | 9 |
| | 0.25 | 3 | 1 | 7 | 7 | 8 | 8 | 8 | 9 | 8 | 9 | 9 | 9 |
| | 0.10 | 1 | 0 | 6 | 6 | 7 | 5 | 8 | 9 | 8 | 9 | 9 | 9 |
| | 0.05 | 0 | 0 | 5 | 4 | 6 | 2 | 8 | 9 | 8 | 9 | 8 | 8 |
| | 0.025 | 0 | 0 | 4 | 2 | 4 | 0 | 8 | 9 | 8 | 7 | 7 | 6 |
| | 0.01 | 0 | 0 | 2 | 0 | 0 | 0 | 8 | 8 | 7 | 5 | 5 | 4 |
| Herbicide/ Dimepiperate | 0.5/5.0 | 4 | 1 | 7 | 7 | 9 | 9 | 8 | 9 | 9 | 9 | 9 | 9 |
| | 0.25/2.5 | 2 | 0 | 7 | 5 | 9 | 9 | 8 | 9 | 9 | 9 | 8 | 9 |
| | 0.10/1.0 | 1 | 0 | 7 | 4 | 9 | 9 | 8 | 9 | 9 | 9 | 8 | 9 |
| | 0.05/0.5 | 0 | 0 | 7 | 4 | 9 | 9 | 8 | 9 | 9 | 8 | 8 | 8 |
| | 0.025/0.25 | 0 | 0 | 6 | 2 | 8 | 7 | 8 | 9 | 8 | 5 | 8 | 7 |
| Dimepiperate alone | 20.0 | 0 | 0 | 5 | 0 | 9 | 9 | 2 | 0 | 9 | 9 | 9 | 9 |
| | 10.0 | 0 | 0 | 4 | 0 | 9 | 9 | 0 | 0 | 9 | 9 | 8 | 8 |
| | 5.0 | 0 | 0 | 2 | 0 | 9 | 9 | 0 | 0 | 8 | 5 | 8 | 8 |
| | 2.5 | 0 | 0 | 1 | 0 | 9 | 9 | 0 | 0 | 8 | 4 | 7 | 6 |
| | 1.0 | 0 | 0 | 0 | 0 | 9 | 9 | 0 | 0 | 4 | 2 | 4 | 2 |
| | 0.5 | 0 | 0 | 0 | 0 | 9 | 9 | 0 | 0 | 0 | 0 | 0 | 0 |
| | 0.25 | 0 | 0 | 0 | 0 | 9 | 7 | 0 | 0 | 0 | 0 | 0 | 0 |
| Check (control) | | 0 | 0 | 0 | 0 | 0 | 0 | 0 | 0 | 0 | 0 | 0 | 0 |

EXAMPLE 4

Evaluation of the safening effect of daimuron and dimepiperate on direct-seeded rice against injury caused by a sulfamoyl urea herbicide Plastic pots, 176 cm² surface area and 16 cm in depth, containing diluvium paddy soil are flooded to the soil surface and the soil and water are paddled to a depth of 2 cm. Twenty germinated rice seeds are sown on the soil surface of each pot and are allowed to grow without flooding conditions until one day prior to test applications. Applications of the herbicide, both alone and in combination with either daimuron or dimepiperate, are made to untreated plants at the 0.5-leaf stage, 1.5-leaf stage and 2.5 leaf stage. After treatment, the water level is maintained at 3 cm above the soil surface throughout the test. The plants are placed on greenhouse benches and cared for in the usual manner. Each test is replicated and no leaching is allowed to occur. Observations are made at 10 and 20 days after treatment and plant injury is evaluated on a 0-9 scale as described in Examples 1 and 2. The sulfamoyl urea herbicide used is 1-{[o-(cyclopropylcarbonyl)phenyl]sulfamoyl}-3-(4,6-dimethoxy-2-pyrimidinyl)urea. The results are averaged and shown in Table IV.

TABLE IV

Safening Effect Of Daimuron And Dimepiperate On Direct-Seeded Rice

| | | Plant Injury | | | | | |
|---|---|---|---|---|---|---|---|
| | | 0.5 leaf DAT | | 1.5 leaf DAT | | 2.5 leaf DAT | |
| Application | Rate kg/ha | 10 | 20 | 10 | 20 | 10 | 20 |
| Herbicide alone | 0.06 | 6.0 | 4.0 | 4.0 | 2.0 | 3.0 | 1.0 |
| Herbicide/ Daimuron | 0.06/1.5 | 4.0 | 2.0 | 3.0 | 1.0 | 1.0 | 0 |
| | 0.06/1.0 | 4.0 | 2.0 | 3.0 | 1.0 | 1.0 | 0 |
| | 0.06/0.6 | 4.0 | 2.0 | 3.0 | 1.0 | 1.0 | 0 |
| | 0.06/0.45 | 4.0 | 2.0 | 3.0 | 1.0 | 1.0 | 0 |
| | 0.06/0.30 | 4.0 | 2.0 | 3.5 | 1.5 | 1.0 | 0 |
| Herbicide/ Dimepiperate | 0.06/3.0 | 8.0 | 8.0 | 3.0 | 1.0 | 1.5 | 0 |
| | 0.06/2.0 | 6.0 | 3.0 | 3.0 | 1.0 | 1.5 | 0 |
| | 0.06/1.35 | 4.0 | 1.0 | 3.0 | 1.0 | 1.5 | 0 |
| Daimuron alone | 1.5 | 0 | 0 | 0 | 0 | 0 | 0 |
| Dimepiperate alone | 3.0 | 8.0 | 8.0 | 1.0 | 0 | 0 | 0 |
| | 2.0 | 7.0 | 5.0 | 0 | 0 | 0 | 0 |
| | 1.35 | 0 | 0 | 0 | 0 | 0 | 0 |
| Check (control) | | 0 | 0 | 0 | 0 | 0 | 0 |

What is claimed is:

1. A method for the protection of a rice crop from injury under conditions whereby crop injury is caused by an herbicidally effective amount of an herbicide of formula I

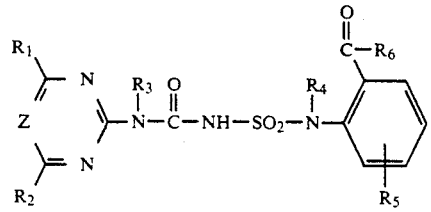

wherein

Z is N or CH;

$R_1$ and $R_2$ are each independently halogen, $C_1-C_6$ alkyl or $C_1-C_6$ alkoxy;

$R_3$ and $R_4$ are each independently hydrogen, $C_1$-$C_6$ alkyl optionally substituted with one to three halogen or $C_1$-$C_4$alkoxy groups, $C_2$-$C_4$ alkenyl and $C_2$-$C_4$alkynyl;

$R_5$ is hydrogen, halogen or $C_1$-$C_4$alkyl optionally substituted with one to three halogens and $R_6$ is $C_1$-$C_6$alkyl or $C_3$-$C_6$cycloalkyl; which comprises applying an effective, non-phytotoxic antidotal amount of a compound selected from the group consisting of 1-($\alpha,\alpha$,-dimethylbenzyl)-3-p-tolylurea and S-(1-methyl-1-phenylethyl)-1-piperidinecarbothioate.

2. The method according to claim 1 wherein Z is CH; $R_1$ and $R_2$ are $C_1$-$C_6$alkoxy and $R_3$, $R_4$ and $R_5$ are hydrogen.

3. The method according to claim 2 wherein $R_6$ is methyl, ethyl or cyclopropyl.

4. The method according to claim 1 wherein the antidote is 1-($\alpha,\alpha$-dimethylbenzyl)-3-p-tolylurea.

5. The method according to claim 4 wherein the herbicide is 1-{[(o-cyclopropylcarbonyl)phenyl]sulfamoyl}-3-(4,6-dimethoxy-2-pyrimidinyl)urea.

6. The method according to claim 1 wherein the antidote is S-(1-methyl-1-phenylethyl)-1-piperidinecarbothioate.

7. The method according to claim 6 wherein the herbicide is 1-{[(o-cyclopropylcarbonyl)phenyl]sulfamoyl}-3-(4,6-dimethoxy-2-pyrimidinyl)urea.

8. The method according to claim 1 wherein the herbicide and the antidote are applied to the water surface of the paddy field from about 4 days before the rice seeds have been sown or the rice plants have been transplanted to about 15 days after the rice seeds have been sown or after the rice plants have been transplanted.

9. The method according to claim 1 wherein the herbicide and the antidote are present at a weight ratio of about 1:2.5 to about 1:150.

10. The method according to claim 1 wherein the herbicide and the antidote are present at a weight ratio of about 1:10 to about 1:50.

11. A rice-safened herbicidal composition which comprises an herbicidally effective amount of an herbicide as described in claim 1, and an antidotally effective amount of a compound selected from the group consisting of 1-($\alpha,\alpha$,-dimethylbenzyl)-3-p-tolylurea and S-(1-methyl-1-phenylethyl)-1-piperidinecarbothioate.

12. The composition according to claim 11 further comprising an agriculturally acceptable diluent.

13. The composition according to claim 12 wherein the diluent is liquid or solid.

14. The composition according to claim 11 wherein the herbicide is 1-{[(o-cyclopropyl)phenyl]sulfamoyl}-3-(4,6-dimethoxy-2-pyrimidinyl)urea.

15. The composition according to claim 11 wherein the herbicide and the antidote are present at a weight ratio of about 1:2.5 to about 1:150.

16. The composition according to claim 11 wherein Z is CH; $R_1$ and $R_2$ are $C_1$-$C_6$ alkoxy and $R_3$, $R_4$ and $R_5$ are hydrogen.

17. The composition according to claim 11 wherein $R_6$ is methyl, ethyl or cyclopropyl.

18. The composition according to claim 14 wherein the antidote is 1-($\alpha,\alpha$-dimethylbenzyl)-3-p-tolylurea.

19. The composition according to claim 14 wherein the antidote is S-(1-methyl-1-phenylethyl)-1-piperidinecarbothioate.

20. The composition according to claim 14 wherein the herbicide and the antidote are present at a weight ratio of about 1:10 to about 1:50.

* * * * *